United States Patent [19]

Elbe et al.

[11] Patent Number: 5,369,124
[45] Date of Patent: Nov. 29, 1994

[54] SUBSTITUTED THIOPHENECARBOXAMIDES

[75] Inventors: Hans-Ludwig Elbe, Wuppertal; Ralf Tiemann; Gerd Hänssler, both of Leverkusen, all of Germany

[73] Assignee: Bayer Aktiengesellschaft, Leverkusen, Germany

[21] Appl. No.: 126,821

[22] Filed: Sep. 24, 1993

[30] Foreign Application Priority Data

Oct. 2, 1992 [DE] Germany ............... 4233198

[51] Int. Cl.$^5$ ............... C07D 333/28; A01N 43/10
[52] U.S. Cl. ............... 514/448; 549/72
[58] Field of Search ............... 549/72; 514/448

[56] References Cited

U.S. PATENT DOCUMENTS

| | | | |
|---|---|---|---|
| 3,243,342 | 3/1966 | Stecker | 549/72 |
| 3,303,201 | 2/1967 | Stecker | 549/72 |
| 5,201,934 | 4/1993 | Muenster et al. | 504/289 |
| 5,244,893 | 9/1993 | Elbe et al. | 514/212 |

FOREIGN PATENT DOCUMENTS 0450355 10/1991 European Pat. Off. .
0423523 4/1994 European Pat. Off. .

OTHER PUBLICATIONS

Chemical Abstracts, vol. 106, 1987, Abst. #18351g, "Chlorophenylfurancarboxamides & Chlorophenylthiophenecarboxamides," Oda et al, JP 61,145,176.

*Primary Examiner*—Gary E. Hollinden
*Assistant Examiner*—Mary C. Cebulak
*Attorney, Agent, or Firm*—Sprung Horn Kramer & Woods

[57] ABSTRACT

Novel substituted thiophenecarboxamides of the formula (I),

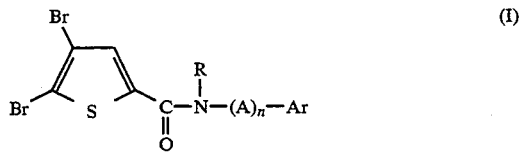

in which
R represents hydrogen or alkyl,
A represents doubly linked alkanediyl,
Ar represents optionally substituted aryl and
n represents a number 0 or 1, with the exception of the compounds 4,5-dibromo-thiophene-2-carboxylic acid N-(4-bromophenyl)-amide, 4,5-dibromo-thiophene-2-carboxylic acid N-(2,3-dichlorophenyl)-amide and 4,5-dibromo-thiophene-2-carboxylic acid N-[2-(3,4-dimethoxyphenyl)-ethyl]-amide, and their use for combating pests.

The novel compounds are described by the formula (I) and they can be prepared by analogous processes, e.g. by reacting suitable thiophenecarbonyl halides with suitable amines.

11 Claims, No Drawings

SUBSTITUTED THIOPHENECARBOXAMIDES

The invention relates to novel substituted thiophenecarboxamides, a process for their preparation and their use in agents for combating pests.

It is known that certain thiophenecarboxamide derivatives, such as, for example, the compound 3-chloro-N-(1-phenylethyl)-benzothiophene-2-carboxamide S,S-dioxide, possess fungicidal properties (cf., e.g., DE-OS (German Published Specification) 38 32 848).

However, the efficacy of these previously known compounds is not completely satisfactory in all areas of application, in particular when low quantities and concentrations are used.

Certain substituted thiophenecarboxamides are additionally known, such as, for example, the compounds 4,5-dibromo-thiophene-2-carboxylic acid N-(4-bromophenyl)-amide (CA reg. no. 15686-72-3), 4,5-dibromo-thiophene-2-carboxylic acid N-(2,3-dichlorophenyl)-amide (CA reg. no. 15950-37-5) and 4,5-dibromo-thiophene-2-carboxylic acid N-[2-(3,4-dimethoxyphenyl)-ethyl]-amide (CA reg. no. 98215-50-0) (cf., e.g., US-PS (US Patent Specification) 3.303,201; GB 10 85 974; J. Chem. Soc. Perkin Trans. I, 275–281 [1985]). At present, nothing is known about whether these compounds have any fungicidal activity.

Novel substituted thiophenecarboxamides of the general formula ( I ) have been found,

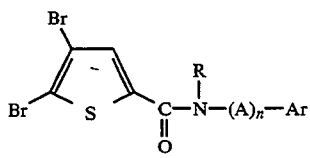

(I)

in which
R represents hydrogen or alkyl,
A represents doubly linked alkanediyl,
Ar represents optionally substituted aryl and
n represents a number 0 or 1,
with the exception of the compounds 4,5-dibromo-thiophene-2-carboxylic acid N-(4-bromophenyl)-amide, 4,5-dibromo-thiophene-2-carboxylic acid N-(2,3-dichlorophenyl)-amide and 4,5-dibromo-thiophene-2-carboxylic acid N-[2-(3,4-dimethoxyphenyl)-ethyl]-amide.

Optionally depending on the nature of the substituents, the compounds of the formula (I) can be present as geometrical and/or optical isomers, or isomeric mixtures of varying composition. Both the pure isomers and the isomeric mixtures are claimed according to the invention.

In addition, it has been found that the novel substituted thiophenecarboxamides of the general formula (I),

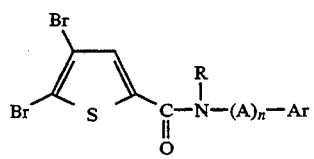

(I)

in which
R represents hydrogen or alkyl,
A represents doubly linked alkanediyl,
Ar represents optionally substituted aryl and
n represents a number 0 or 1,
with the exception of the compounds 4,5-dibromo-thiophene-2-carboxylic acid N-(4-bromophenyl)-amide, 4,5-dibromo-thiophene-2-carboxylic acid N-(2,3-dichlorophenyl)- amide and 4,5-dibromo-thiophene-2-carboxylic acid N-[2-(3,4-dimethoxyphenyl)-ethyl]-amide are obtained if thiophenecarbonyl halides of the formula (II),

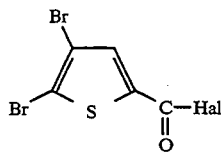

(II)

in which
Hal represents halogen,
are reacted with amines of the formula (III),

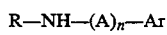

R—NH—(A)$_n$—Ar (III)

in which
R, A, Ar and n have the abovementioned meaning,
optionally in the presence of a diluent and optionally in the presence of a reaction auxiliary.

Finally, it has been found that the novel substituted thiophenecarboxamides of the general formula (I) possess good activity against pests.

Surprisingly, the substituted thiophenecarboxamides of the general formula (I) according to the invention exhibit substantially superior activity against plant-damaging microorganisms as compared with the thiophene-carboxamide derivatives known from the state of the art, such as, for example, the compound 3-chloro-N-(1-phenylethyl)-benzothiophene-2-carboxamide S,S-dioxide, which are compounds which are closely related chemically and/or with regard to their action.

R represents straight-chain or branched alkyl; preferably straight-chain or branched alkyl having 1 to 8 carbon atoms; particularly preferably having 1 to 4 carbon atoms.

A represents doubly linked alkanediyl; preferably straight-chain or branched, doubly linked alkanediyl having 1 to 8 carbon atoms; particularly preferably straight-chain or branched, doubly linked alkanediyl having 1 to 4 carbon atoms.

Ar represents phenyl which is optionally substituted identically or differently once to more than once, preferably phenyl which is unsubstituted or substituted identically or differently once to five times; particularly preferably phenyl which is unsubstituted or substituted identically or differently once to three times.

Ar also represents naphthyl.

The substituted thiophenecarboxamides according to the invention are generally defined by the formula (I). Compounds of the formula (I) are preferred in which
R represents hydrogen or straight-chain or branched alkyl having 1 to 8 carbon atoms,
A represents straight-chain or branched, doubly linked alkanediyl having 1 to 8 carbon atoms,
Ar represents phenyl which is optionally substituted identically or differently once to more than once, suitable substituents being: halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoxyiminoalkyl having in each case 1 to 4 carbon atoms in the individual alkyl moieties, as well as phenyl, which is optionally substituted identically or differently once or more than once by halogen, straight-chain or branched alkyl, straight-chain or branched alkoxy, straight-chain or branched halogenoalkyl and straight-chain or branched halogenoalkoxy having in each case 1 to 4 carbon atoms and optionally 1 to 9 identical or different halogen atoms, and n represents a number 0 or 1, with the exception of the compounds 4,5-dibromo-thiophene-2-carboxylic acid N-(4-bromophenyl)-amide, 4,5-dibromo-thiophene-2-carboxylic acid N-(2,3-dichlorophenyl)-amide and 4,5-dibromo-thiophene-2-carboxylic acid N-[2(3,4-dimethoxyphenyl)-ethyl]-amide.

Compounds of the formula (I) are particularly preferred in which

R represents hydrogen or straight-chain or branched alkyl having 1 to 4 carbon atoms, A represents straight-chain or branched, doubly linked alkanediyl having 1 to 4 carbon atoms, Ar represents phenyl which is optionally substituted identically or differently once to five times or once to three times, suitable substituents being: fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoxyiminomethyl, methoxyiminoethyl, ethoxyiminomethyl, ethoxyiminoethyl or phenyl, which is optionally substituted identically or differently once to three times by fluorine, chlorine, bromine, methyl, ethyl, n- or i-propyl, methoxy, ethoxy, trifluoromethyl and/or trifluoromethoxy, and n represents a number 0 or 1, with the exception of the compounds 4,5-dibromo-thiophene-2-carboxylic acid N-(4-bromophenyl)-amide, 4,5-dibromo-thiophene-2-carboxylic acid N-(2,3-dichlorophenyl)-amide and 4,5-dibromo-thiophene-2-carboxylic acid N-[2(3,4-dimethoxyphenyl)-ethyl]-amide.

Compounds of the formula (I) are very particularly preferred in which

R represents hydrogen or methyl,

A represents doubly linked methylene or ethylene,

Ar represents phenyl which is optionally substituted identically or differently once to three times, suitable substituents being: fluorine, chlorine, bromine, methyl, ethyl, methoxy, ethoxy, methylthio, methylsulphonyl, trifluoromethyl, trifluoromethoxy, trifluoromethylthio or trifluoromethylsulphonyl and n represents a number 0 or 1, with the exception of the compounds 4,5-dibromo-thiophene-2-carboxylic acid N-(4-bromophenyl)-amide, 4,5-dibromo-thiophene-2-carboxylic acid N-(2,3-dichlorophenyl)amide and 4,5-dibromo-thiophene-2-carboxylic acid N-[2-(3,4-dimethoxyphenyl)-ethyl]-amide.

The compounds of the general formula (I) which may be mentioned individually are those listed in the Preparation Examples.

If, for example, 4,5-dibromo-thiophene-2-carbonyl chloride and 3,4-dimethylaniline are used as starting compounds, the course of the reaction of the process according to the invention can be represented by the following formula diagram:

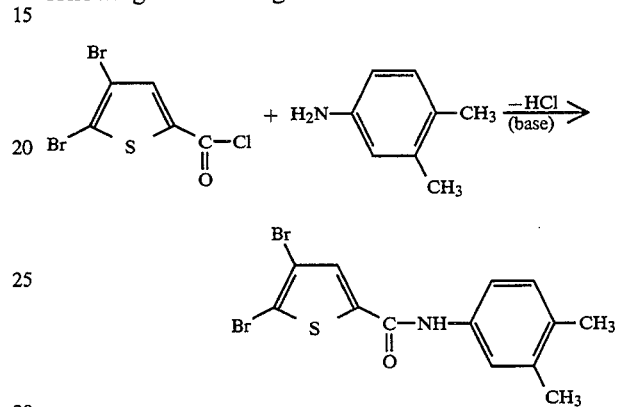

The thiophenecarbonyl halides which are required as starting substances for carrying out the process according to the invention are generally defined by the formula (II). In this formula (II), Hal preferably represents chlorine or bromine.

The thiophenecarbonyl halides of the formula (II) are known (cf., e.g., EP 450 355; US-PS (US Patent Specification) 3.303.201; DE 12 01 952; GB 10 85 974).

The amines which are additionally required as starting substances for carrying out the process according to the invention are generally defined by the formula (III). In this formula (III), R, A, Ar and n preferably represent those radicals and indices which have already been mentioned, in connection with the description of the compounds of the formula (I) according to the invention, as being preferred for these substituents and this index number.

The amines of the formula (III) are well-known compounds of organic chemistry or can be obtained in analogy to well-known processes.

Inert organic solvents are suitable diluents for carrying out the process according to the invention. These include, in particular, aliphatic, alicyclic or aromatic, optionally halogenated, hydrocarbons, such as, for example, benzinc, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, or sulphoxides, such as dimethyl sulphoxide.

The process according to the invention is preferably carried out in the presence of a suitable reaction auxiliary. All customary inorganic or organic bases are suitable for this purpose. These include, for example, hydrides, hydroxides, amides, alcoholares, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, sodium acetate, potassium acetate, calcium acetate, sodium carbonate, potassium carbonate, potassium hydrogen carbonate, sodium hydrogen carbonate or ammonium compounds, such as ammonium hydroxide, ammonium acetate, ammonium carbonate or ammonium hydrogen carbonate, as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The process according to the invention can optionally also be carried out in a two-phase system, such as, for example, water/toluene or water/dichloromethane, optionally in the presence of a suitable phase-transfer catalyst. Examples of such catalysts which may be mentioned are: tetrabutylammonium iodide, tetrabutylammonium bromide, tetrabutylammonium chloride, tributyl-methyl-phosphonium bromide, trimethyl-$C_{13}$/$C_{15}$-alkylammonium chloride, trimethyl-$C_{13}$/$C_{15}$-alkylammonium bromide, dibenzyl-dimethyl-ammonium methyl sulphate, dimethyl-$C_{12}$/$C_{14}$ -alkyl-benzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

In carrying out the process according to the invention, the reaction temperatures may be varied over a relatively wide range. In general, temperatures of between −20° C. and 150° C., preferably temperatures of between 0° C. and 120° C., are employed.

The process according to the invention is usually carried out under atmospheric pressure. However, it is also possible to employ elevated or reduced pressure.

For carrying out the process according to the invention, 1.0 to 5.0 mol, preferably 1.0 to 2.5 mol, of amine of the formula (III), and optionally 1.0 to 5.0 mol, preferably 1.0 to 2.5 mol, of base used as a reaction auxiliary, are generally employed per mol of thiophenecarbonyl halide of the formula (II). The performance of the reaction, the working up and the isolation of the reaction products takes place according to well-known processes (cf., in this context, the Preparation Examples as well).

The purification of the end products of the formula (I) is effected using customary processes, for example by column chromatography or by recrystallisation.

Characterisation is effected using the melting point or, in the case of non-crystallising compounds, using the refractive index or proton nuclear magnetic resonance spectroscopy ($^1$H-NMR).

The active compounds according to the invention exhibit strong action against pests, and may be employed in practice for combating unwanted pernicious organisms. The active compounds are suitable for use as agents for protecting plants, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for or example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *podosphaera leucotricha;*

Venturia species, such as, for example, *Venturia inaequalis;*

Pyrenophora species, such as, for example, *pyrenophora teres* or *Pyrenophora graminea* (conidia forth: Drechslera, synonym: Helminthosporium);

Cochliobolus species, such as, for example, *Cochliobolus sativus* (conidia form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;* pyricularia species, such as, for example, *pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Lepto-sphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention may be employed particularly successfully for combating diseases in the cultivation of fruit and vegetables, as for example against the causative agent of apple powdery mildew (*Podosphaera leucotricha*), or for combating diseases of rice, as for example against the causative agent of rice blast disease (*Pyricularia oryzae*). In addition, the active compounds according to the invention also possess resistance-inducing activity.

Depending on their particular physical and/or chemical properties, the active compounds can be converted to the customary formulations, such as solutions, emulsions, suspensions, powders, foes, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water; by liquefied gaseous extenders or carriers are meant liquids which are gaseous at normal temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumhen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations contain in general between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low-volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

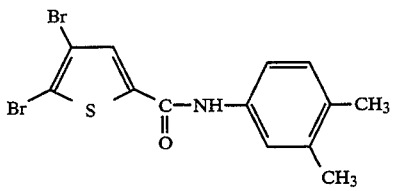

A solution of 6.0 g (0.02 mol) of 4,5-dibromothiophene-2-carbonyl chloride is added, at room temperature and while stirring, to 2.0 g (0.02 mol) of triethylamine and 2.4 g (0.02 mol) of 3,4-dimethylaniline in 30 ml of toluene, and the mixture is subsequently heated at 50° C. for 2 hours. For the working up, the reaction mixture is cooled down to room temperature, the mixture is added to water, and the precipitated solid is filtered off with suction and subsequently washed with water and n-hexane, and the residue is dried at 50° C. in vacuo.

6.4 g (82% of theory) of 4,5-dibromothiophene-2-carboxylic acid N-(3,4-dimethylphenyl)-amide are obtained with a melting point of 216–217° C.

The following substituted thiophenecarboxamides of the general formula (I) are obtained in a corresponding manner and in accordance with the general preparation instructions:

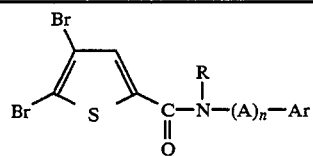

(I)

| Example no. | R | Ar | A | n | Physical properties |
|---|---|---|---|---|---|
| 2 | H | 4-F-C6H4 | — | 0 | m.p. 182–184° C. |
| 3 | H | 4-OCF3-C6H4 | — | 0 | m.p. 150–151° C. |
| 4 | H | 3,4,5-(CH3)3-C6H2 | — | 0 | m.p. 204–206° C. |
| 5 | H | 2,3-(CH3)2-C6H3 | — | 0 | m.p. 213–215° C. |
| 6 | H | C6H5 | CH2 | 1 | m.p. 125° C. |
| 7 | H | 4-Cl-C6H4 | — | 0 | m.p. 202–204° C. |
| 8 | H | 3-Cl-5-CH3-C6H3 | — | 0 | m.p. 163–165° C. |
| 9 | H | 4-CH3-C6H4 | — | 0 | m.p. 185–187° C. |
| 10 | H | 3,4-Cl2-C6H3 | — | 0 | m.p. 154–156° C. |
| 11 | H | 3-CH3-4-Cl-C6H3 | — | 0 | m.p. 137–138° C. |

-continued

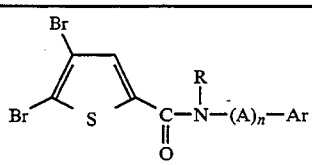

(I)

| Example no. | R | Ar | A | n | Physical properties |
|---|---|---|---|---|---|
| 12 | H | 2-OCH3-C6H4 | — | 0 | m.p. 102° C. |
| 13 | H | 3,5-(CH3)2-C6H3 | — | 0 | m.p. 122–124° C. |
| 14 | H | C6H5 | — | 0 | 1H-NMR*): 8.07 (1H) |

*)The 1H-NMR spectra were recorded in deuterochloroform (CDCl3) or hexadeuterodimethyl sulphoxide (DMSO-d6) using tetramethylsilane (TMS) as the internal standard. The chemical shift is given as the δ value in ppm.

APPLICATION EXAMPLES

In the following Application Examples, the compound cited below was employed as the comparison substance:

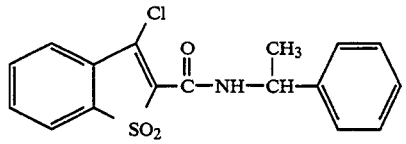

3-Chloro-N-(1-phenylethyl)-benzothiophene-2-carboxamide S,S-dioxide (known from DE-OS (German Published Specification) 38 32 848)

EXAMPLE A

Pyricularia test (rice)/protective
Solvent: 12.5 parts by weight of acetone
Emulsifier: 0.3 part by weight of alkyl-aryl polyglycol ether To produce a suitable preparation of active compound, one part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae.

The plants are then placed in a greenhouse at 25° C. and 100% relative atmospheric humidity.

Evaluation of the disease infestation is carried out 4 days after the inoculation.

At a concentration of active compound of 0.025%, the compounds according to Preparation Examples 6, 13 and 14, show a degree of activity of at least 90% as compared with the untreated control, whereas the degree of activity for the comparison substance is only 10%.

What is claimed is:

1. A substituted thiophenecarboxamide of the formula

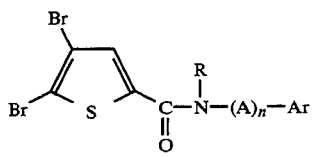

in which

R represents hydrogen or methyl,

A represents doubly linked methylene or ethylene,

Ar represents phenyl which is optionally substituted identically or differently once to three times, suitable substituents being selected from the group consisting of: fluorine, chlorine, bromine, methyl, ethyl, methoxy, ethoxy, methylthio, methylsulphonyl, trifluoromethyl, trifluoromehoxy, trifluoromethylthio or trifluoromethylsulphonyl and n represents a number 0 or 1, with the exception of the compounds 4,5-dibromothiophene-2-carboxylic acid N-(4-bromophenyl)-amide, 4,5-dibromo-thiophene-2-carboxylic acid N-(2,3-dichlorophenyl)-amide and 4,5-dibromothiophene-2-carboxylic acid N-[2-(3,4-dimethoxyphenyl)-ethyl]-amide.

2. A compound according to claim 1, wherein such compound is 4,5-dibromothiophene-2-carboxylic acid N-(2,3,5-trimethylphenyl)-amide of the formula

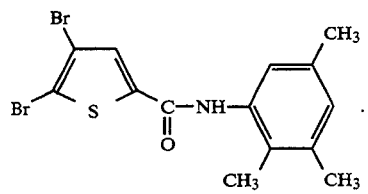

3. A compound according to claim 1, wherein such compound is 4,5-dibromothiophene-2-carboxylic acid N-(benzyl)-amide of the formula

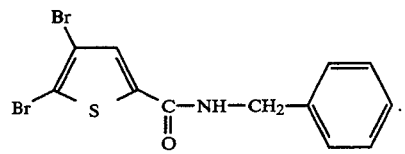

4. A compound according to claim 1, wherein such compound is 4,5-dibromothiophene-2-carboxylic acid N-(4-chlorophenyl)-amide of the formula

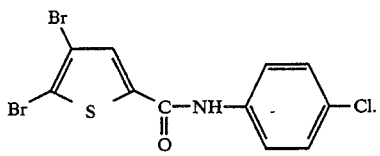

5. A compound according to claim 1, wherein such compound is 4,5-dibromothiophene-2-carboxylic acid N-(2,4-dichlorophenyl)-amide of the formula

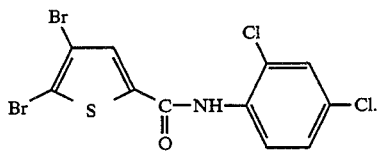

6. A compound according to claim 1, wherein such compound is 4,5-dibromothiophene-2-carboxylic acid N-(2-chloro-5-methylphenyl)-amide of the formula

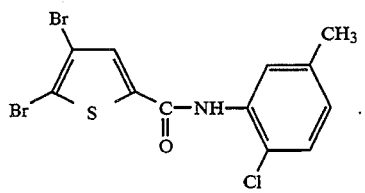

7. A compound according to claim 1, wherein such compound is 4,5-dibromothiophene-2-carboxylic acid N-(3-methoxyphenyl)-amide of the formula

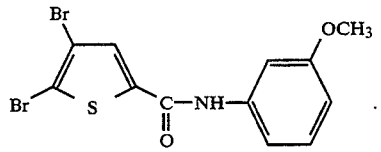

8. A compound according to claim 1, wherein such compound is 4,5-dibromothiophene-2-carboxylic acid N-(2,4-dimethylphenyl)-amide of the formula

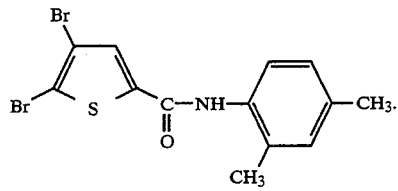

9. A method of combating fungi, which method comprises applying to such fungi or to their habitat a fungicidally effective amount of a compound according to claim 1.

10. A fungicidal composition comprising a fungicidally effective amount of a compound according to claim 1 and an inert diluent.

11. A method according to claim 9, wherein such compound is 4,5-dibromothiophene-2-carboxylic acid N-(2,3,5-trimethylphenyl)-amide or 4,5-dibromothiophene-2-carboxylic acid N-(benzyl)-amide or 4,5-dibromothiophene-2-carboxylic acid N-(4-chlorophenyl)-amide or 4,5-dibromothiophene-2-carboxylic acid N-(2,4-dichlorophenyl)-amide or 4,5-dibromothiophene-2-carboxylic acid N-(2-chloro-5-methylphenyl)-amide or 4,5-dibromothiophene-2-carboxylic acid N-(3-methoxyphenyl)-amide or 4,5-dibromothiophene-2-carboxylic acid N-(2,4-dimethylphenyl)-amide.

* * * * *